United States Patent [19]

Tokura

[11] Patent Number: 5,192,983
[45] Date of Patent: Mar. 9, 1993

[54] APPARATUS FOR AND METHOD OF CHECKING EXTERNAL APPEARANCE OF SOLDERING STATE

[75] Inventor: Nobufumi Tokura, Fukuoka, Japan

[73] Assignee: Matsushita Electric Industrial Co., Ltd., Osaka, Japan

[21] Appl. No.: 626,051

[22] Filed: Dec. 13, 1990

[30] Foreign Application Priority Data

Dec. 19, 1989 [JP] Japan ............................. 1-330754
Oct. 9, 1990 [JP] Japan ............................. 2-271094

[51] Int. Cl.⁵ ..................... G01B 11/24; G01N 21/00
[52] U.S. Cl. ................................. 356/376; 356/237
[58] Field of Search .............. 356/394, 237, 375, 376; 378/58; 358/106, 107

[56] References Cited

FOREIGN PATENT DOCUMENTS 0154949  6/1988  Japan ................................. 356/394
63-177042 7/1988 Japan .
63-177045 7/1988 Japan .

OTHER PUBLICATIONS

Geise et al, "A Laser Scaner for PC Board Inspection," Electronic Packaging and Production, vol. 20, #12, Dec. 1980.

Primary Examiner—F. L. Evans
Assistant Examiner—K. P. Hantis
Attorney, Agent, or Firm—Lowe, Price, LeBlanc & Becker

[57] ABSTRACT

A laser beam is projected from above toward a solder fillet for bonding the corresponding one of leads of an electronic component to a circuit board. The laser beam is reflected by the solder fillet, and the reflected beam is received by light receiving means disposed above and aslant the leads, thereby to measure a shape of the solder fillet.

6 Claims, 5 Drawing Sheets

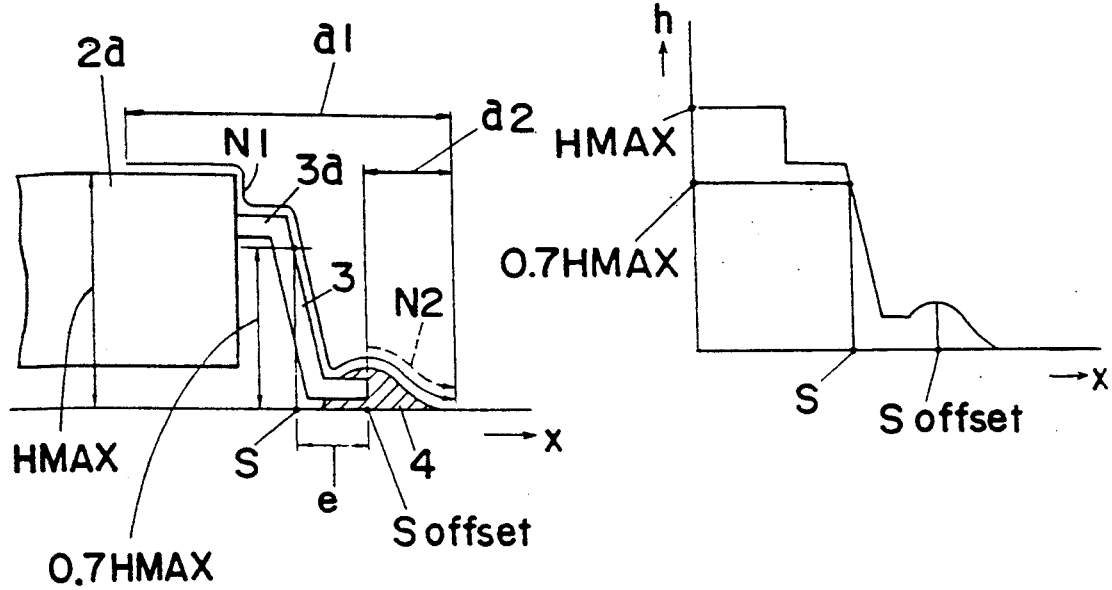
FIG. 5
FIG. 6
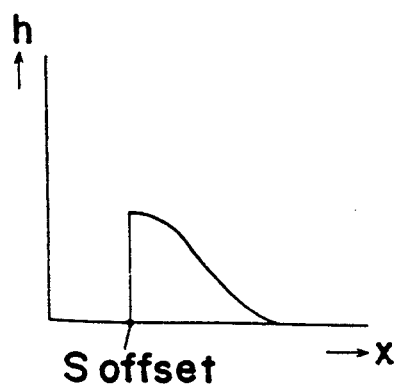
FIG. 7
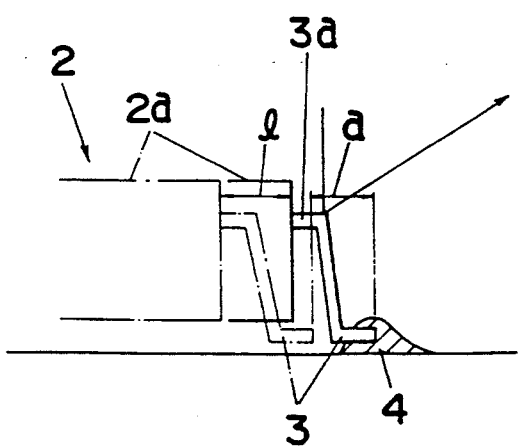
FIG. 8

5,192,983

APPARATUS FOR AND METHOD OF CHECKING EXTERNAL APPEARANCE OF SOLDERING STATE

BACKGROUND OF THE INVENTION

The present invention relates to an apparatus for and a method of checking the external appearance of a soldering state. More particularly, it relates to expedients for reliably and exactly measuring the shape of a solder fillet formed at the distal end of a lead, by the scanning of a laser beam.

Various expedients for checking the external appearance of a soldering state by the use of a laser beam have heretofore been proposed (refer to, for example, the official gazettes of Japanese Patent Applications Laid-open No. 177042/1988 and No. 177045/1988).

In any of the prior-art expedients, however, technical problems to be stated below, which are important for the check of the external appearance of a soldering state based on the projection of a laser beam remain unsolved.

Especially important in the soldering state is the shape of a solder fillet which is formed at the distal end of a lead. Whether the soldering state is accepted or rejected, is greatly affected by the quality of the shape of the solder fillet. In judging the acceptance or rejection of the soldering state, accordingly, naturally the laser beam must infallibly hit the solder fillet which is an object to be measured. In this regard, an electronic component placed on a circuit board involves a positional deviation, a dimensional error or the like relative to the designed position thereof. Therefore, even when the designed position is given by teaching beforehand so as to project the laser beam toward this designed position, the laser beam does not always hit the solder fillet. Particularly in recent years, the pitches of leads have a tendency to become very narrow in compliance with requirements for high densities of integration and packaging, and there are leads of small pitches less than 3 mm. When such a lead involves a slight positional deviation, even the projection of the laser beam toward the taught position results in irradiating a spot other than the solder fillet to-be-measured, and hence, an erroneous measured result is obtained.

Moreover, the solder fillet is made of a lustrous metal such as tin or lead and has a mirror-like surface, and it is substantially angled in its vertical section. Accordingly, unless a direction in which the laser beam is projected and a position at which light receiving means receives reflected light are contrived, the reflected light cannot be precisely received, so that a measured result becomes incorrect. It is the actual circumstances that expedients for reliably projecting the laser beam on the solder fillet and for reliably receiving the laser beam reflected by the solder fillet as described above have not been established yet.

SUMMARY OF THE INVENTION

The present invention therefore has for its object to provide the aforementioned expedients for solving the technical problems peculiar to the check of the external appearance of a soldering state, that is, the expedients capable of reliably projecting a laser beam on a solder fillet to-be-checked and reliably receiving reflected light from the solder fillet.

In order to accomplish the object, according to the present invention, an apparatus for checking an external appearance of an electronic component is constructed comprising laser projection means for scanning a laser beam from above leads toward a solder fillet which is formed at a distal end of each of the leads extended out of a mold member of the electronic component mounted on a circuit board, and light receiving means for receiving the laser beam reflected by the solder fillet, at a position which is above the leads and aslant a direction orthogonally intersecting to an extending direction of the lead.

With the above construction, the laser light is scanned with respect to the lead in a direction traversing this lead, and the laser beam reflected by the lead is received, thereby to detect the center of this lead. Subsequently, the laser beam is projected while being scanned in the extending direction of the lead so as to pass through the detected center, thereby to project the laser beam on the solder fillet to-be-checked. In addition, the laser beam reflected from the solder fillet is received by the light receiving means which is disposed above the leads and aslant the direction orthogonal to the extending direction of the leads. Thus, the shape of the solder fillet is measured.

BRIEF DESCRIPTION OF THE DRAWINGS

FIG. 5 is a side view for explaining another aspect of performance of the present invention;

FIGS. 6 and 7 are graphs each showing a measured result in the aspect of FIG. 5;

FIG. 8 is a side view of the chip of a minitransistor;

PREFERRED EMBODIMENTS OF THE INVENTION

Now, the embodiments of the present invention will be described with reference to the drawings.

EMBODIMENT 1

Figure 1:
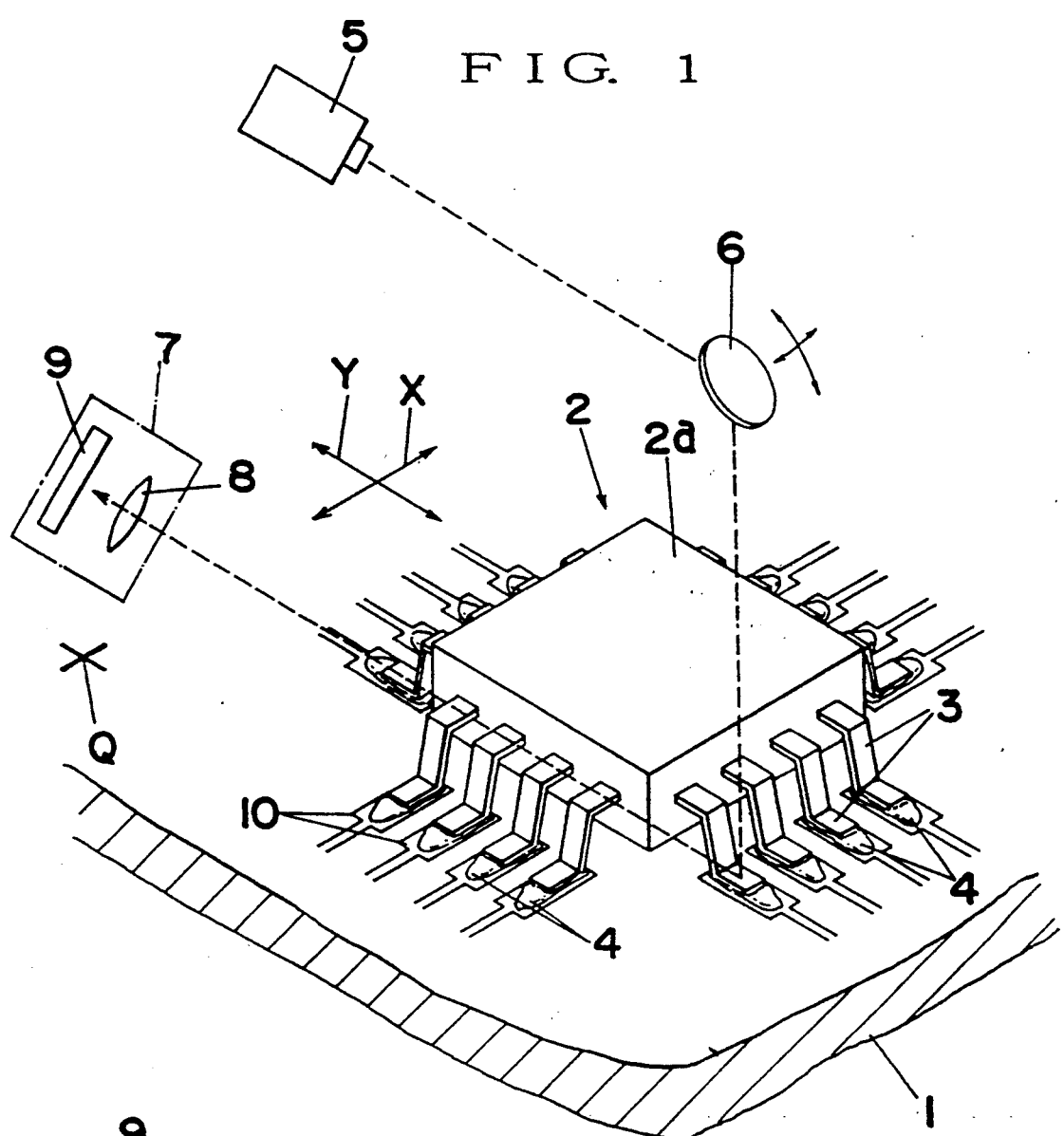
FIG. 1 is a perspective view of an apparatus for checking the external appearance of a soldering state.

FIG. 1 is a perspective view of an apparatus for checking the external appearance of a soldering state. Numeral 1 designates a circuit board, on the upper surface of which an electronic component (hereinbelow, termed "chip") 2 is mounted. Numeral 3 indicates each of a large number of leads which are extended out sidewards from the mold member 2a of the chip 2, and numeral 4 each of solder fillets which are formed at the distal ends of the leads 3.

Numeral 5 indicates a laser device. The light spot of a laser beam emerging from this laser device is reflected by a mirror 6 so as to irradiate the solder fillet 4, and the reflected light thereof from the solder fillet 4 enters light receiving means 7. On that occasion, the laser beam is projected while being scanned in X- and Y-directions by rotating the mirror 6 in two directions. The light receiving means 7 includes a focusing element such as convex lens 8, and a position sensor such as PSD (positioning sensitive device) 9. In the figure, the laser beam is depicted by an arrow in a broken line.

Figure 2:
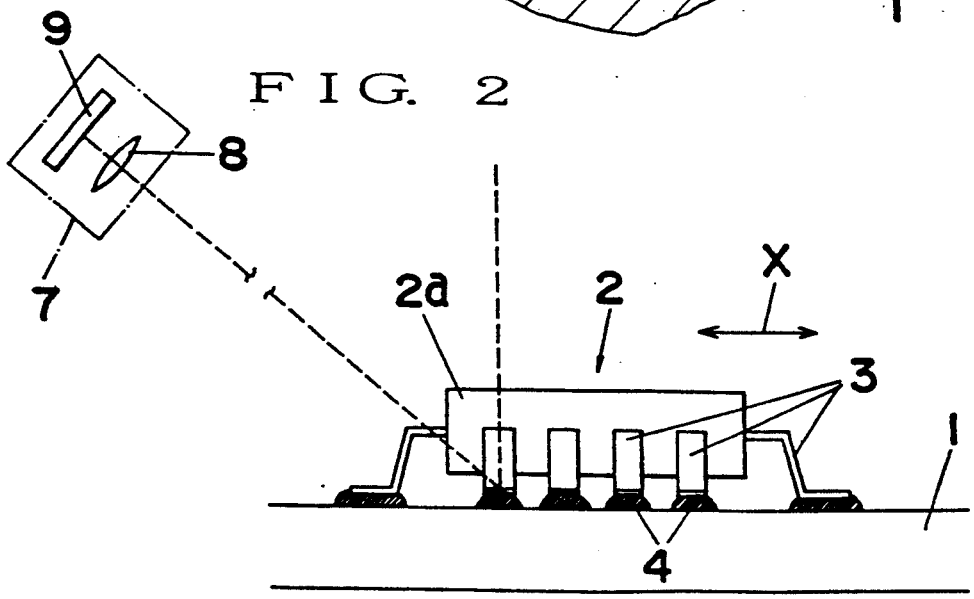
FIGS. 2, 3 and 4 are a front view, a partial perspective view and a plan view for explaining the proceeding of a measurement, respectively.
Figure 3:
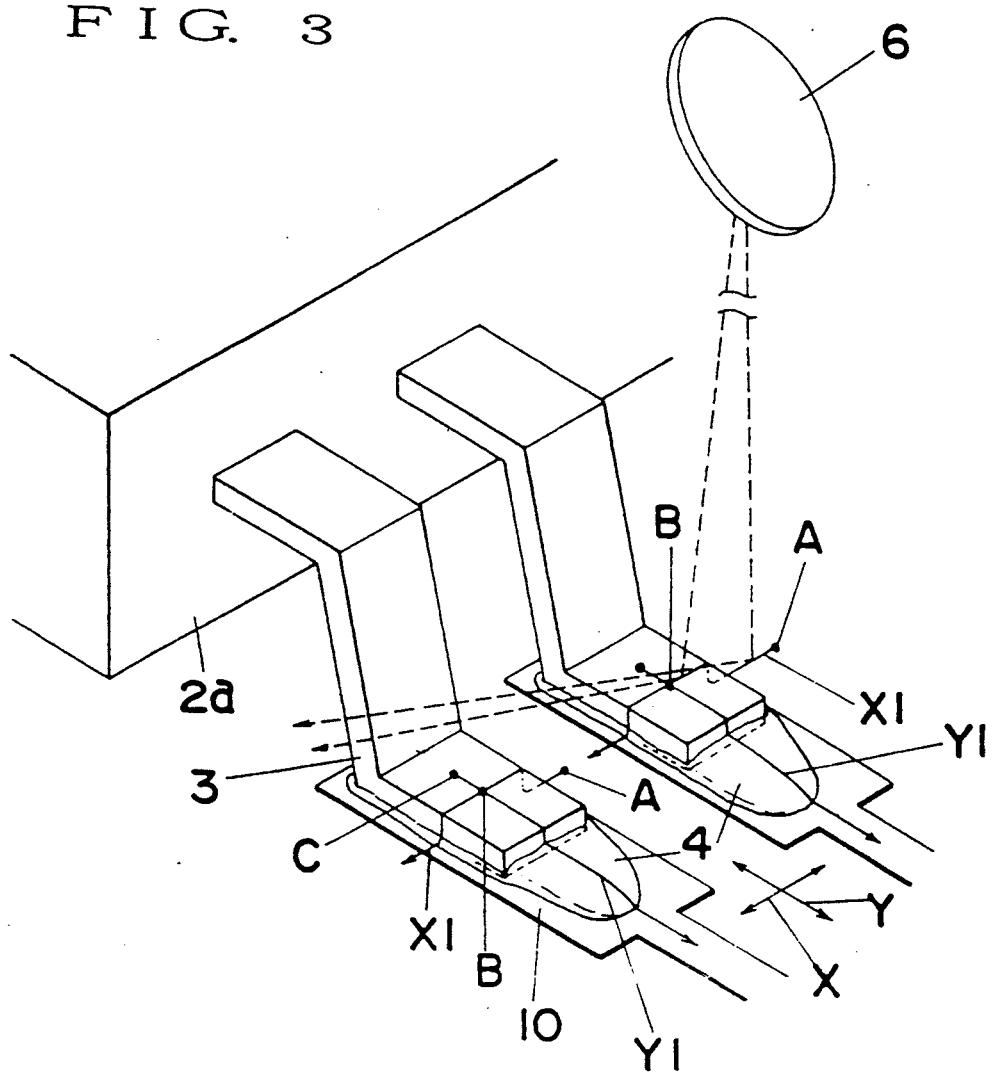

As shown in FIGS. 2 and 3, the laser beam reflected by the mirror 6 is projected from above the leads 3 and solder fillets 4. In addition, the light receiving means 7 is arranged above the leads 3 and aslant the X-direction orthogonally intersecting to the extending direction of the leads 3 (the Y-direction). By setting the projection direction of the laser beam and the arrangement position of the light receiving means 7 in this manner, it is permitted to stably and reliably receive the laser beam reflected by the solder fillet 4 which has a mirror-like surface and which is angled in its vertical section. In FIG. 1, numeral 10 denotes each of lands in a circuit pattern formed on the circuit board 1, and letter Q denotes one of positional reference marks formed on the suitable parts of the upper surface of the circuit board 1. The coordinate positions of the individual lands 10 relative to the mark Q are known.

The apparatus is constructed as described above, and a method of checking the external appearance of a soldering state will now be described.

Figure 4:
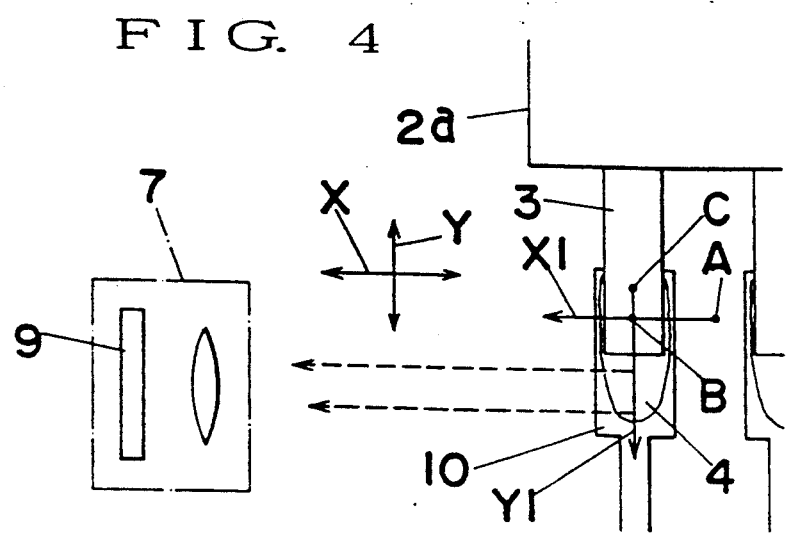
Figure 9:
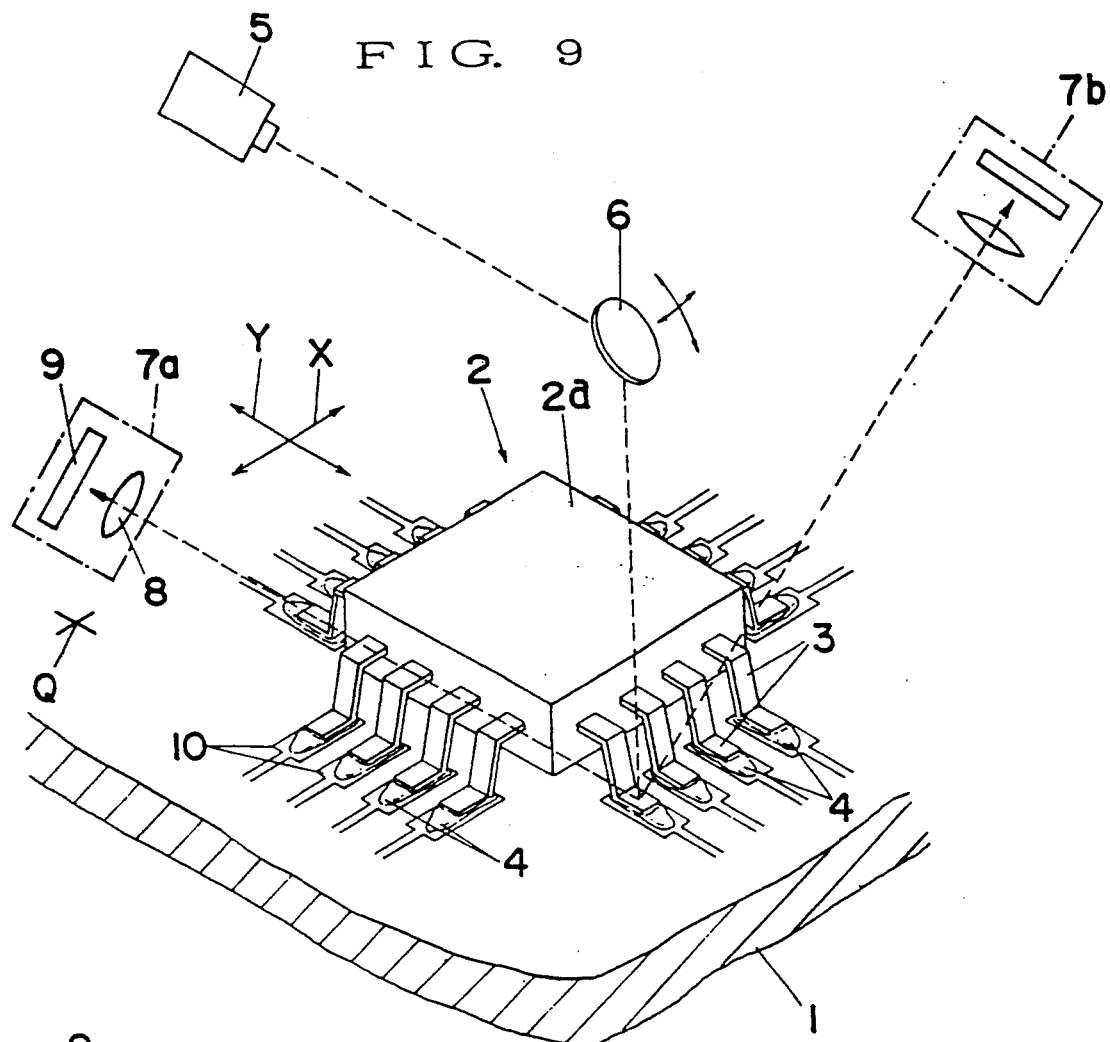
FIG. 9 is a perspective view of an apparatus for checking the external appearance of a soldering state in another embodiment.
Figure 10:
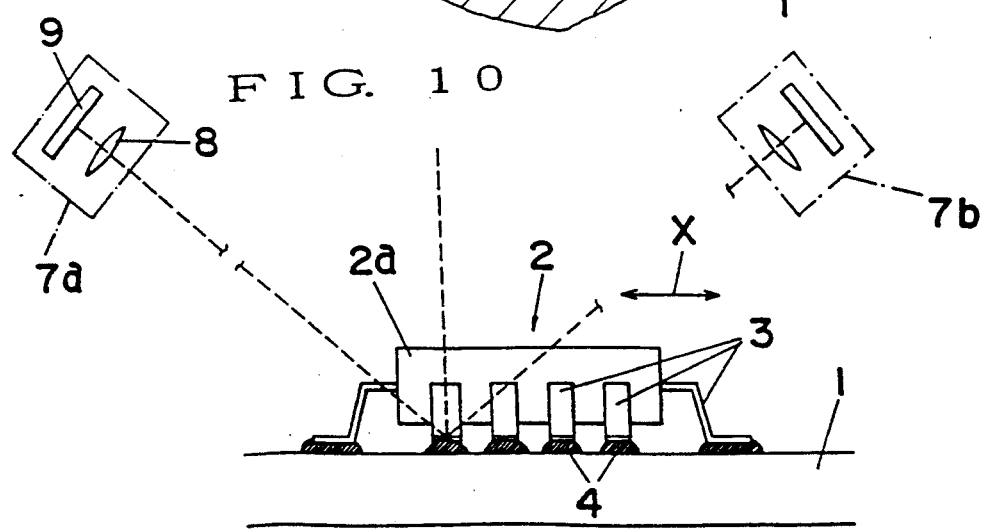
FIGS. 10, 11 and 12 are a front view, a plan view and a characteristic diagram of reflected light concerning the embodiment of FIG. 9, respectively.
Figure 11:
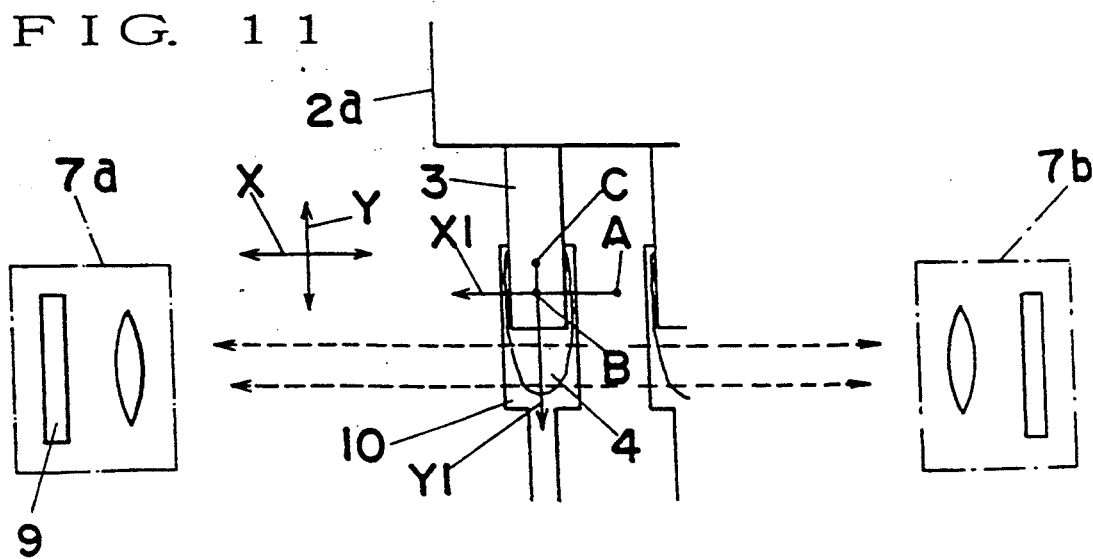

Referring to FIGS. 3 and 4, a start point A is first set sideways of the lead 3, and the laser beam is scanningly projected therefrom in a direction X1 traversing the lead 3. The laser beam reflected from the lead 3 is received by the light receiving means 7, thereby to detect the widthwise center B of the lead 3. The detection of the center B is done every lead 3. The start point A is set sideways of each of the lands 10 whose positions relative to the positional reference mark Q of the circuit board 1 are known as described before. Subsequently, another start point C is set on a Y-directional line passing through the center B, and the laser beam is scanningly projected in the extending direction (direction Y1) of the lead 3, thereby to measure the shape of the solder fillet 4.

In this manner, with the method, the widthwise center B of the lead 3 is first detected, and the laser beam is subsequently projected in the extending direction of the lead 3 so as to pass through the center B. Therefore, even when the chip 2 has a positional deviation in the X-direction thereof, the laser beam can hit the solder fillet 4 without fail. Moreover, the light receiving means 7 is disposed at the position above the lead 3 and aslant the direction orthogonal to the extending direction of the lead 3. Therefore, the light reflected by the solder fillet 4 after the projection of the laser beam on this solder fillet 4 from above can be received by the light receiving means 7 reliably and stably.

Meanwhile, in some of chips, for example, a minitransistor depicted in FIG. 8, the lead 3 is bent at an abrupt slope along the side wall of the mold member 2a of the chip 2. Regarding such a chip, let's consider a case where the shape of the solder fillet 4 is measured by scanning and projecting the laser beam along a predetermined measurement area a in the Y-direction. In this case, when the chip 2 involves a positional deviation of length l in the Y-direction, the laser beam is reflected by the shoulder 3a of the lead 3, and the height of the shoulder 3a is misrecognized as the maximum height of the solder fillet 4. In the figure, dot-and-dash lines indicate the state of the chip 2 free from the positional deviation. Such misjudgements are prone to arise, not only in the minitransistor, but also in a chip having leads of abrupt slope, such as a tantalum capacitor or coil, and a chip having long leads extended out sideways, such as a QFP (quad flat package) or SOP (small out-line package). Accordingly, there will now be described an expedient which can project the laser beam infallibly on the solder fillet even when the Y-directional positional deviation is involved in this manner.

In FIG. 5, it is assumed that the chip 2 involves a Y-directional positional deviation of considerable value. Here is set a measurement area a1 which is large enough to cover an extent from the upper surface of the mold member 2a or the upper surface of the base end 3a of the lead 3 to the outer end of the solder fillet 4. The first scanning projection of the laser beam is carried out along the area a1, thereby to measure the external appearance of the chip 2 in the area a1. Symbol N1 denotes a scanning line on this occasion.

FIG. 6 shows the result of the first measurement. In the figure, symbol HMAX denotes the height of the upper surface of the chip 2. A spot S whose height (for example, 0.7 HMAX) is at a predetermined ratio (0.7) to the obtained height HMAX, is found. Subsequently, an offset spot $S_{offset}$ is set at a position which is a predetermined offset distance e away from the spot S toward the outer end of the solder fillet 4. Next, an area a2 for the second measurement is set so as to extend from the offset spot $S_{offset}$ to the side of the outer end of the solder fillet 4. As the second measurement, the laser beam is scanned and projected from a start point corresponding to the offset spot $S_{offset}$, as indicated by an arrow of broken line N2 in FIG. 5, thereby to measure the shape of the solder fillet 4 in detail. FIG. 7 shows the result of the second measurement.

Thus, according to this method, even when the chip 2 has the positional deviation in the Y-direction, the solder fillet (the part extended at a downward slope from the distal end of the lead) which is very important for judging the acceptance or rejection of the soldering state can be reliably irradiated with the laser beam and can have its shape reliably measured. The aforementioned numerical values of 0.7, e etc. are set beforehand in accordance with the kind of chip and the required accuracy of the shape.

The check of the external appearance of the soldering state should desirably be performed at the highest possible speed over the largest possible extent. In this regard, the method illustrated in FIGS. 5 thru 7 has the demerit of expending a long time because the operation of scanningly projecting the laser beam must be carried out twice. Therefore, the first scanning projection which is done in order to determine the start point of the measurement area a2 for the second measurement is executed coarsely (at, for example, 2 mm/100 points), and the second scanning projection which is done in order to measure the shape of the solder fillet in detail is executed finely (at, for example, 0.5 mm/100 points), whereby the checking speed can be raised.

EMBODIMENT 2

FIGS. 9 thru 12 illustrate the second embodiment of the present invention, in which light receiving means 7a and 7b in the number of two are respectively disposed at left-hand and right-hand positions above and aslant leads 3.

There will now be explained the reason why the light receiving means 7a and 7b numbering two are arranged on both the sides.

Figure 12:
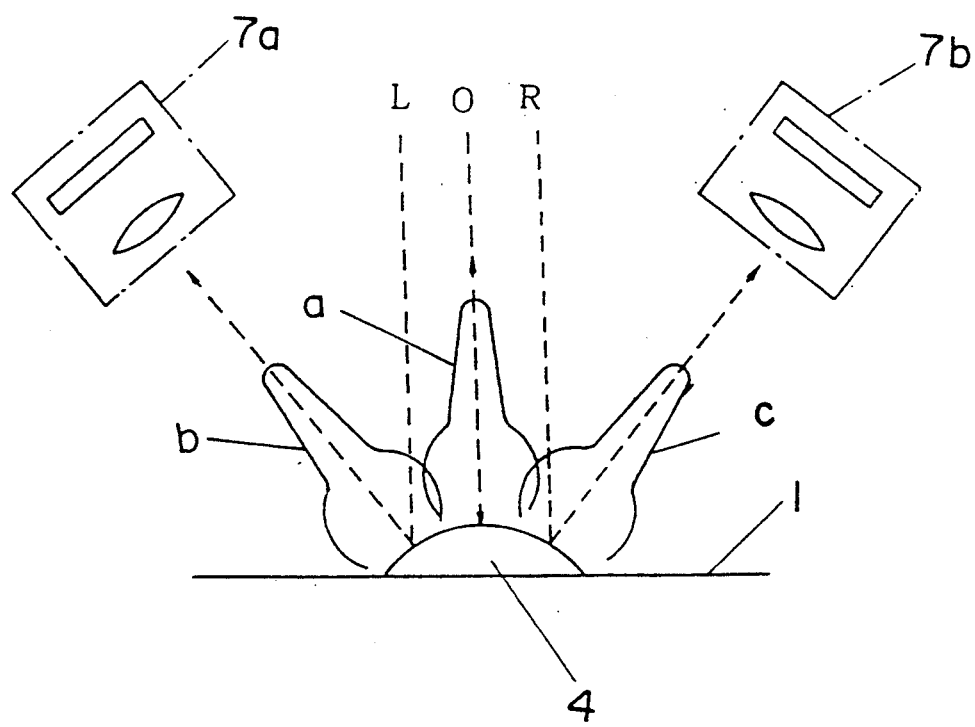

Referring to FIG. 12, a laser beam is not always projected on the widthwise center 0 of a solder fillet 4, but it is sometimes projected on the left part L or right part R of the solder fillet 4. Causes for the eccentric projection are the drift of the laser beam, the positional deviation and deformation of the solder fillet 4, etc. In the figure, letters a, b and c indicate the directivities of reflected light beams.

When the laser beam is projected on the center O, the resulting reflected light enters the left-hand and right-hand light receiving means 7a, 7b in equal amounts, and hence, the shape of the solder fillet 4 can be computatively estimated from the outputs of the light receiving means 7a, 7b. In this case, the shape may be estimated from the output of either of the light receiving means 7a, 7b, or it may well be estimated from the average value of the outputs of both the light receiving means 7a, 7b.

When the laser beam is projected on the left part L, the resulting reflected light enters the left-hand light receiving means 7a sufficiently, but it hardly enters the right-hand light receiving means 7b. In this case, accordingly, the shape of the solder fillet 4 is computatively estimated from the output of the left-hand light receiving means 7a which receives the larger amount of light. Likewise, when the laser beam is projected on the right part R, the shape of the solder fillet 4 is computatively estimated from the output of the right-hand light receiving means 7b which receives the larger amount of light.

In this manner, with the provision of the light receiving means 7a and 7b at the left-hand and right-hand positions above and aslant the leads 3, the shape of the solder fillet 4 can be measured by receiving the reflected light by means of either of the light receiving means 7a and 7b, even when the laser beam is projected on the left part L or right part R.

As described above, according to the present invention, even when an electronic component involves a positional deviation in an X-direction or a Y-direction, a laser beam can be scanned reliably on a solder fillet, and the resulting reflected light can be received reliably, whereby the shape of the solder fillet can be precisely measured.

What is claimed is:

1. A method of checking an external appearance of a soldering fillet; comprising the steps of scanning a laser beam on one of a plurality of leads extended sideways from a mold member of an electronic component mounted on a circuit board, in a direction traversing the lead, and receiving the laser beam reflected by the lead, thereby to detent a widthwise center of the lead by light receiving means, scanning the laser beam in an extended direction of the lead so as to pass through the detected center of the lead and thereby to project the laser beam on the solder fillet, and receiving resulting reflected light by light receiving means which is disposed at a position above the lead and aslant a direction intersecting orthogonally to the extended direction of the lead, so as to measure a shape of a solder fillet.

2. A method of checking an external appearance of a soldering fillet; comprising the steps of scanning a laser beam on one of a plurality of leads of an electronic component mounted on a circuit board, in a direction traversing the lead, and receiving the laser beam reflected by the lead, thereby to detect a widthwise center of the lead, and subsequently, projecting the laser beam in an extended direction of the lead so as to pass through the center, and receiving resulting reflected light by a plurality of light receiving means which are disposed at right-hand and left-hand positions above and aslant the leads, so as to measure a shape of a solder fillet.

3. In a method of checking an external appearance of a soldering state wherein a laser beam is scanned toward a solder fillet, and resulting reflected light is detected by light receiving means; a method of checking an external appearance of a soldering state of the solder fillet characterized by comprising the steps of scanning the laser beam from an upper surface of a mold member of an electronic component or an upper surface of a base end of a lead of the electronic component toward an outer end of the solder fillet, so as to detect a spot which has a height at a predetermined ratio to a height of the electronic component, and also to set an offset point at a position which is a predetermined offset distance away from the detected spot toward the outer end of the solder fillet, and subsequently, scanning the laser beam again toward the outer end of the solder fillet with a start point at the offset point, thereby to measure a shape of the solder fillet.

4. An apparatus for checking soldered connections of electrical component leads which comprises:
    means for scanning a laser beam onto a soldered lead in first and second directions in which the first direction is transverse both to the second direction and the soldered lead;
    means for receiving first reflected light produced by laser light directed onto the soldered lead along said first direction and determining therefrom the position of the widthwise center of the soldered lead, said second direction in which said laser beam is scanned
    onto the soldered lead is along a direction in which the soldered lead extends, so that said laser beam scanned in said second direction passes through the determined widthwise center of the soldered lead and produces a second reflected light; and
    means for receiving the second reflected light produced by laser light directed onto said soldered lead from said second direction and measuring therefrom the shape of a soldered connection of the soldered lead.

5. An apparatus for checking soldered connections of electrical component leads according to claim 4, wherein said means for receiving the second reflected light comprises two light detectors.

6. An apparatus for checking soldered connections of electrical components comprising:
    means for scanning a laser beam onto a soldered lead in first and second directions in which the first direction is in a direction in which the lead extends;
    means for receiving first reflected light produced by laser light directed onto the soldered lead along said first direction and detecting therefrom a spot on the soldered lead which has a height that is a predetermined ratio of the height of the electrical component from which the soldered lead extends, said second direction in which said laser beam is scanned
    onto the soldered lead is in the direction in which the soldered lead extends from a position that is a set distance from the detected spot to the end of a soldered connection of the soldered lead so as to produce a second reflected light; and
    means for receiving the second reflected light produced by laser light directed onto said soldered lead from said second direction and determining therefrom the shape of the soldered connection.

* * * * *